(12) United States Patent
Faiola et al.

(10) Patent No.: US 8,645,164 B2
(45) Date of Patent: Feb. 4, 2014

(54) MEDICAL INFORMATION VISUALIZATION ASSISTANT SYSTEM AND METHOD

(75) Inventors: Anthony Faiola, Indianapolis, IN (US); Simon C. Hillier, Etna, NH (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 152 days.

(21) Appl. No.: 12/789,267

(22) Filed: May 27, 2010

(65) Prior Publication Data

US 2011/0004071 A1    Jan. 6, 2011

Related U.S. Application Data

(60) Provisional application No. 61/217,200, filed on May 28, 2009.

(51) Int. Cl.
*G06F 19/00* (2011.01)

(52) U.S. Cl.
USPC .......................................................... 705/3

(58) Field of Classification Search
USPC ........... 705/2, 3; 715/700; 600/509; 713/186; 707/10
See application file for complete search history.

(56) References Cited

U.S. PATENT DOCUMENTS

| 2006/0265249 | A1* | 11/2006 | Follis et al. ........................ 705/3 |
| 2008/0281831 | A1* | 11/2008 | Mindrum ......................... 707/10 |
| 2009/0055735 | A1* | 2/2009 | Zaleski et al. ................. 715/700 |
| 2009/0287103 | A1* | 11/2009 | Pillai ............................. 600/509 |
| 2010/0185871 | A1* | 7/2010 | Scherrer et al. ............... 713/186 |

OTHER PUBLICATIONS

Faiola, et al, Multivariate Relational Visualization of Complex Clinical Datasets in a Critical Care Setting: A Data Visualization Interactive Prototype, (2006) Proceedings of the HCI Symposium—10th Information Visulatization Conference, IEEE Publishing, London England.

* cited by examiner

*Primary Examiner* — John Pauls
(74) *Attorney, Agent, or Firm* — Ryan O. White; Taft, Stettinius & Hollister, LLP

(57) ABSTRACT

Methods, systems, devices and/or apparatus related to displaying and visualizing medical information for facilitating effective analysis by medical professionals. Example systems for displaying medical information related to a human subject may include a computer system, server system(s), data monitoring device(s), electronic medical record/interoperability tool, medical information database(s) and a medical information visualization tool having an interface, software and management database(s). Such system may simultaneously output at least two medical parameters (relating to near real-time medical information and historical medical information) to a display device using the medical information visualization tool.

16 Claims, 11 Drawing Sheets

MEDICAL INFORMATION VISUALIZATION ASSISTANT SYSTEM AND METHOD

CROSS REFERENCE TO RELATED APPLICATIONS

This application claims the benefit of U.S. Provisional Patent Application Ser. No. 61/217,200, entitled "Medical Information Visualization Assistant System and Method," filed on May 28, 2009, the disclosure of which is incorporated herein by reference.

BACKGROUND

The intensive care unit (ICU) of a medical facility may be a data rich environment. ICU patients usually have significant organ system derangement and may have very little physiologic reserve. Effective medical care may require intensive monitoring of organ function, frequent multimodal diagnostic testing, and many consultations from subspecialty physicians and other health care providers. In this kind of a critical care environment, it is often difficult to make rapid evaluations of a patient's condition due to the overwhelming volume of data that is continuously generated. Sources of patient-generated data may include continuous automatic physiologic monitoring and intermittently determined data that is gathered by bedside care providers and/or from various diagnostic testing sources. In addition to patient-generated data, there may be vast arrays of clinical data generated that document the treatment received by the patient. This data may include drug therapy, respiratory therapy, physical therapy and/or all other clinical interventions.

Effective clinical decisions pertaining to the care of these patients may be made when physicians can easily organize and understand the vast flood of data from these various sources. Unfortunately, physicians and other health care staff typically have to retrieve this critical data from multiple locations and organize it into a cohesive profile of the patient's current condition. Furthermore, the data retrieved from these diverse sources is usually presented in a form that does not allow trends and relationships between co-variables to be immediately recognized. Further, critical care physicians (CCP) work in a highly stressful environment and are usually pressed for time, frequently looking after several critically ill patients. As a result, the process of monitoring, evaluating and treating complex medical problems is labor intensive and time-consuming; it demands that physicians analyze data in text and numeric form.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

Figure 1:
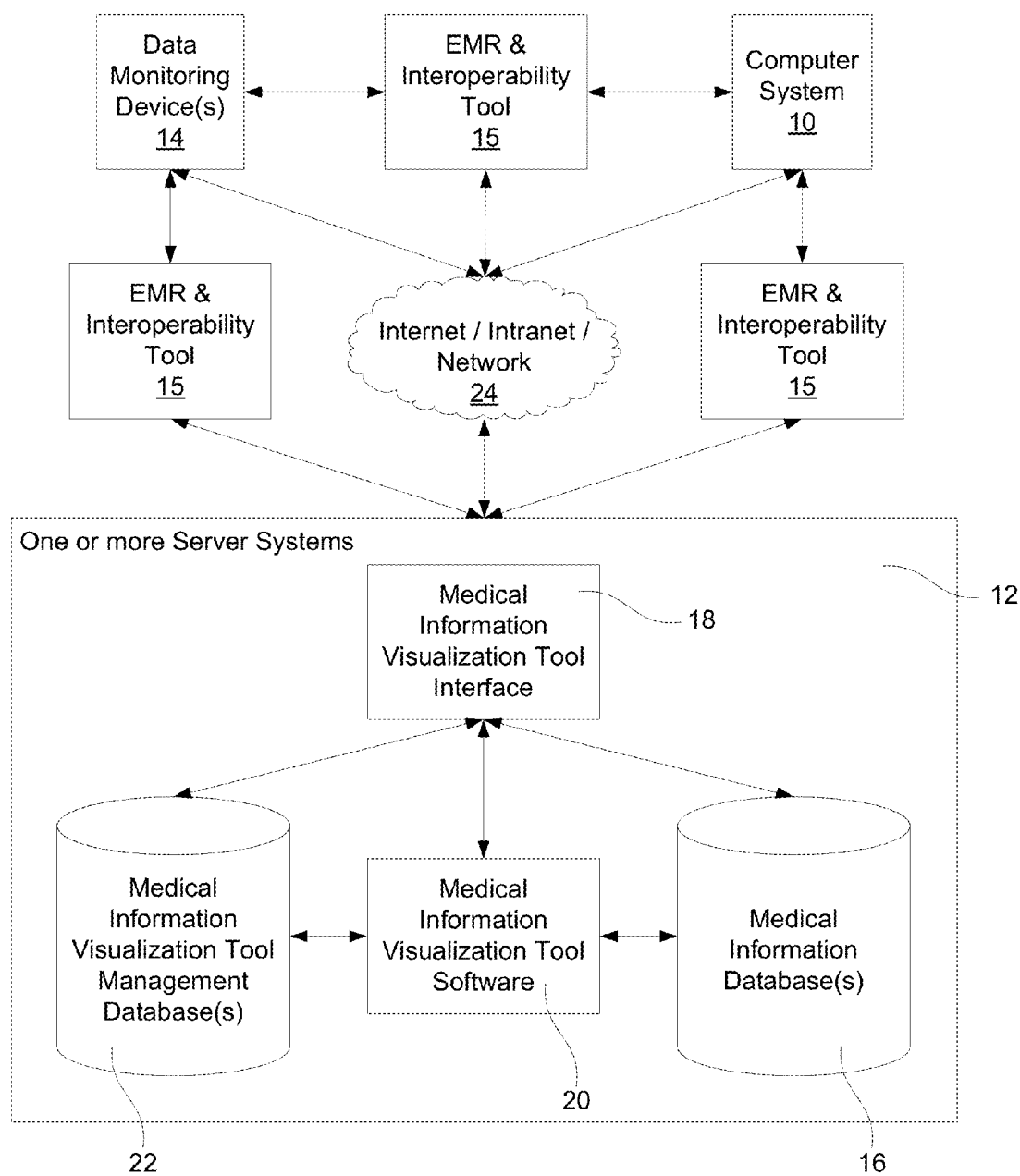
FIG. 1 is a diagram depicting an exemplary embodiment of the present invention.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

This disclosure is drawn to methods and systems related to displaying and visualizing medical information for facilitating effective analysis by medical professionals. While an exemplary embodiment may be utilized in an intensive care unit of a medical facility, any aspect of medical care (such as a psychiatric facility, general practice environments and home-based medical care, for example) may utilize the methods and systems described herein. Further, although the methods and systems are generally described herein in relation to medical care, other industries (such as the automotive and manufacturing industries, for example) may utilize the methods and systems.

Medical data visualization (MDV) may provide valuable assistance for data analysis and decision making for critical care physicians (CCPs). How CCPs perceive and interact with patient data may affect their ability to arrive at the best critical care solution. The medical field has provided excellent opportunities for the application of data visualization technology with the potential to help improve healthcare that can improve health-related outcomes. In a real-life critical care context, the clinical decision making process should always be supported by relevant and reliable clinical data. In this case, the use of MDV may be considered a data analysis method in which physicians are able to select the relevant variables to model and decide on representation or encoding of factors to better obtain the analysis results and draw conclusions.

In an exemplary embodiment (as shown in FIG. 1), a system for displaying medical information related to a human subject is provided. This system may include a computer system 10, server system(s) 12, data monitoring device(s) 14, electronic medical record (EMR) storage/interoperability tool 15, medical information database(s) 16 and a medical information visualization tool including an interface 18, software 20 and management database(s) 22. The computer system 10, server system(s) 12, the data monitoring devices 14, the EMR storage/interoperability tool 15, and the medical information database(s) 16 may be in communication with each other directly, indirectly and/or via a network connection 24 (such as the Internet, an intranet or other network). The data monitoring devices 14 may monitor the human subject to measure, record and/or transmit medical information associated with the human subject. The medical information may be transmitted to the EMR storage/interoperability tool 15 and/or medical information database(s) 16 for storage. Each EMR 15 and/or medical information database 16 may be configured to store medical information associated with the human subject. The medical information visualization tool may be stored on the server system(s) 12 and may be accessible by the computer system 10 and/or the data monitoring device(s) 14. Further, the medical information visualization tool may be configured to display the medical information (including medical parameters related to clinical data and/or human subject-generated data). The medical information visualization tool may be configured to simultaneously display near real-time medical information from the data monitoring devices 14 and historical medical information from the medical information databases 16. In some embodiments, the historical medical information may be displayed on a graph having a dynamically adjustable time period.

In some embodiments, the EMR 15 may be utilized with an interoperability tool 15. The interoperability tool 15 may allow medical information to be received and/or shared in a compatible format with computer system 10, server system(s) 12, data monitoring device(s) 14, electronic medical record (EMR) storage/interoperability tool 15, medical information database(s) 16 and the medical information visualization tool. Example interoperability tools 15 may include open source tools such as those available from Mirth Corporation, among others.

Data monitoring devices 14 may include any type of device configured to monitor and/or measure medical information. Examples of such data monitoring devices 14 may include devices that monitor pulse oximetry, mixed venous oximetry, intracranial pressure, neuro-physiologic data, spontaneous potential, evoked potential, aortic echocardiography, laser Doppler perfusion, Bair Hugger temperature and venous compression devices, among others. Data monitoring devices 14 may monitor, measure and or record medical information in the form of parameters and/or settings used by the data monitoring devices 14 and/or in the form of parameters measured in response to the data monitoring devices 14. For example, a drug dispensing device may monitor the dispensing rate of a drug being provided to a patient as one parameter, and also monitor the patient's blood pressure in response to the drug being administered as another parameter. In such an example, both parameters may be displayed by the medical information visualization tool.

In one embodiment, the medical information visualization tool may include an information visualization timeline (IVT) 28. The IVT 28 may provide historical data to the health care clinician in the form of a plurality of horizontal graphs 30 of the data (where the time parameter 32 is the horizontal axis and the medical data parameter range 34 is the vertical axis) in controllable time resolutions. Clinicians may be able to select a range of physiological parameters of the patient, viewing them side-by-side in clinical context (in the present embodiment, the plurality of graphs 30 are organized in a vertical side-by-side, or stacked, relationship). In one embodiment, this may include up to five or six parameter histories or timeline graphs 30. Some embodiments may include limitless parameter histories or timeline graphs 30. These parameter histories or timeline graphs 30 may be stacked (or customized) on a touch-screen display any way the clinician prefers (e.g. using a drag-and-drop system). In some embodiments, the parameter histories or timeline graphs 30 may be displayed horizontally, vertically, diagonally and in other similar orientations. Within each timeline graph 30, data points 36 may identify the data reading extracted from a patient monitoring system. Data points 36 may be located in varying increments on the scale of each physiological parameter reading, depending on the time resolution. Colored (or grayed) areas may indicate a safe zone 38 for the parameter (or may alternatively indicate a danger or warning zone), if applicable. Each timeline graph 30 may have its own dedicated scale, (as shown on the left side in FIGS. 4 and 5, for example). At the bottom of the IVT 28, a timeline 32 may indicate the hours and minutes within each day.

Figure 4:
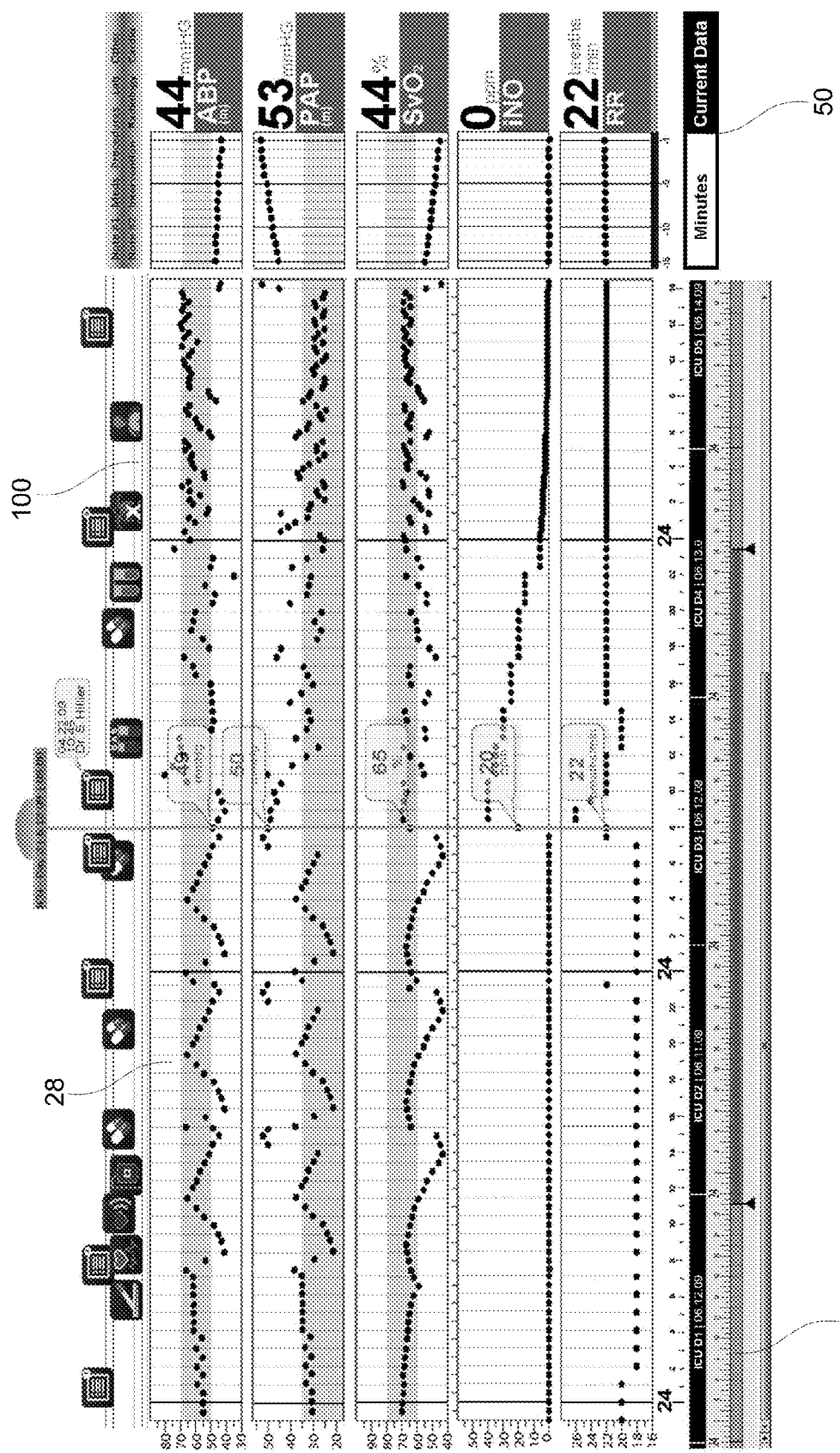
FIG. 4 is a diagram depicting another exemplary embodiment of the present invention.
Figure 5:
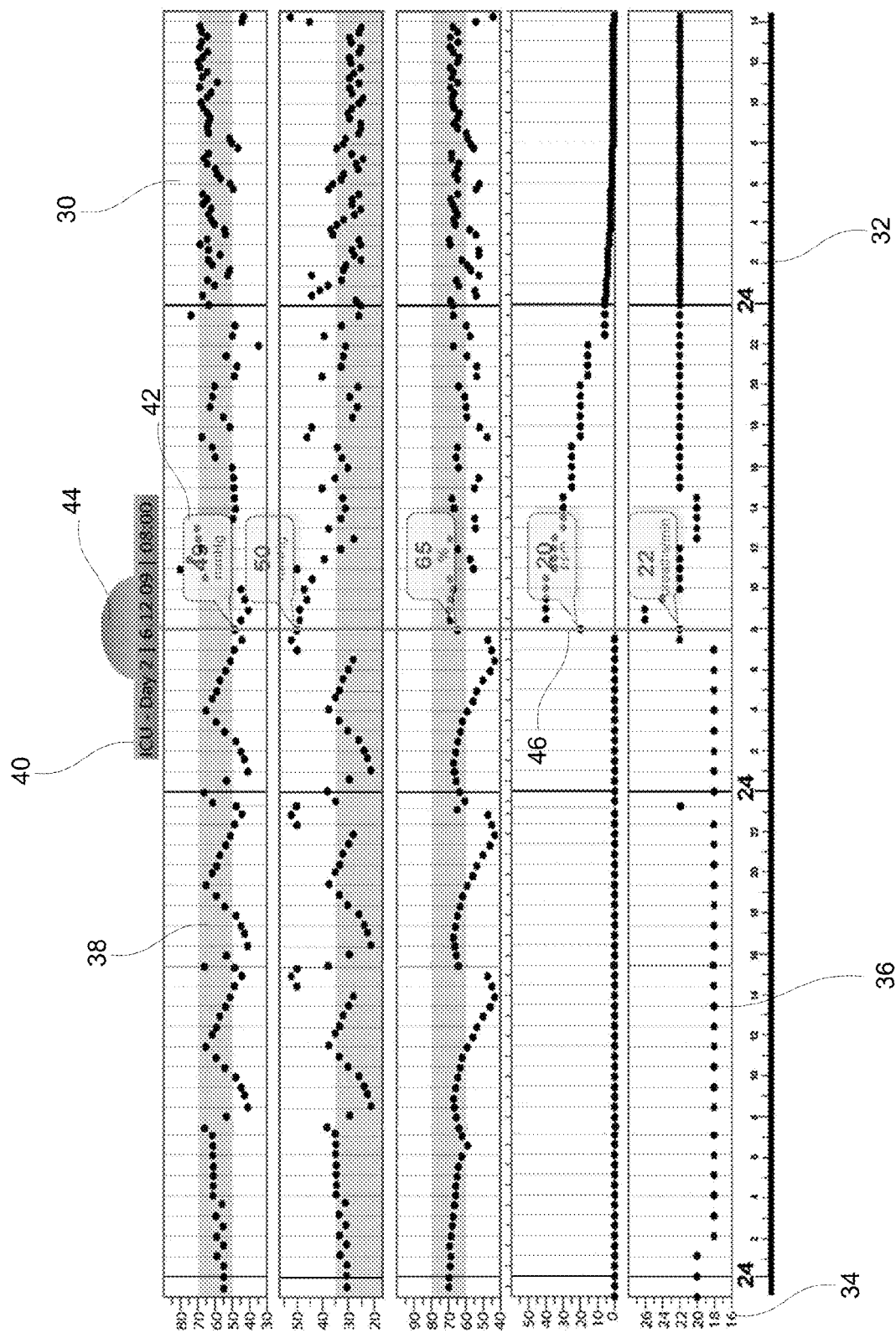
FIG. 5 is a diagram depicting even another exemplary embodiment of the present invention.

In one embodiment, the medical information visualization tool may be configured to display the historical medical information on a timeline graph 30 (as shown in FIG. 4 generally and FIG. 5 in more detail). The graph 30 may represent a particular medical parameter during the dynamically adjustable time period. In another embodiment, the medical information visualization tool may be configured to be dynamically adjustable such that the medical parameters may be displayed in a customizable order. For example, medical parameters including heart rate, blood oxygen level and blood pressure may be arranged (stacked) in many ways (e.g. heart rate, blood pressure, then blood oxygen level, etc.). In yet another embodiment, the medical parameters may be displayed in a vertical orientation.

In another embodiment (as shown in FIG. 4 generally and FIG. 5 in more detail), the medical information visualization tool may include a scrubber tool 40 configured to select a particular time on a timeline 32 and to display the historical medical information associated with the particular time on a graph 30. The graph 30 may represent predetermined medical parameter(s). In FIG. 5, for example, these parameters may include ABP, PAP, SvO, iNO and RR. Further, the medical information visualization tool may display numeric values 42 associated with the historical medical information associated with the particular time. In FIG. 5, for example, these numeric values 42 include ABP=49 mmHg, PAP=50 mmHg, SvO=65%, iNO=20 ppm and RR=22 breaths/min. In one embodiment, the scrubber tool 40 may be further configured to be moved along the timeline 32 using the touch-screen (by touching the scrubber handle 44 and sliding it to the desired position on the timeline 32). In such an embodiment, the medical information visualization tool may display numeric values 42 associated with the historical medical information associated with the scrubber tool's 40 location on the timeline.

In some cases, clinicians may want to know all the exact parameter readings at a particular point on the timeline 32 relative to the current (real-time) reading (which may be indicated to the far right in FIG. 4, for example). The scrubber tool 40 may be moved, using the touch-screen display, by a touch-and-slide action on the scrubber handle 44 near the top of the scrubber tool 40. The scrubber tool 40 may be flagged on the top of the graphs 30, with the current time readings, that indicate the specific information for that location on the timeline graph 30 (e.g., day in the ICU, time in minutes and seconds, and date). The scrubber tool 40 may also include a data point scrubber (DPS) 46. The DPS 46 may allow the clinician to scrub or move the tool 40 back and forth along the timeline 32 to any data point 36 (corresponding to a particular time), helping the clinician see the specific parameter values at that point in time. Data balloons 42 (as shown in FIGS. 4 and 5) may be transparent so as not to hide any data points 36. Further, the data balloons 42 may disappear after a predetermined amount of time (e.g. 10 seconds).

Figure 6:
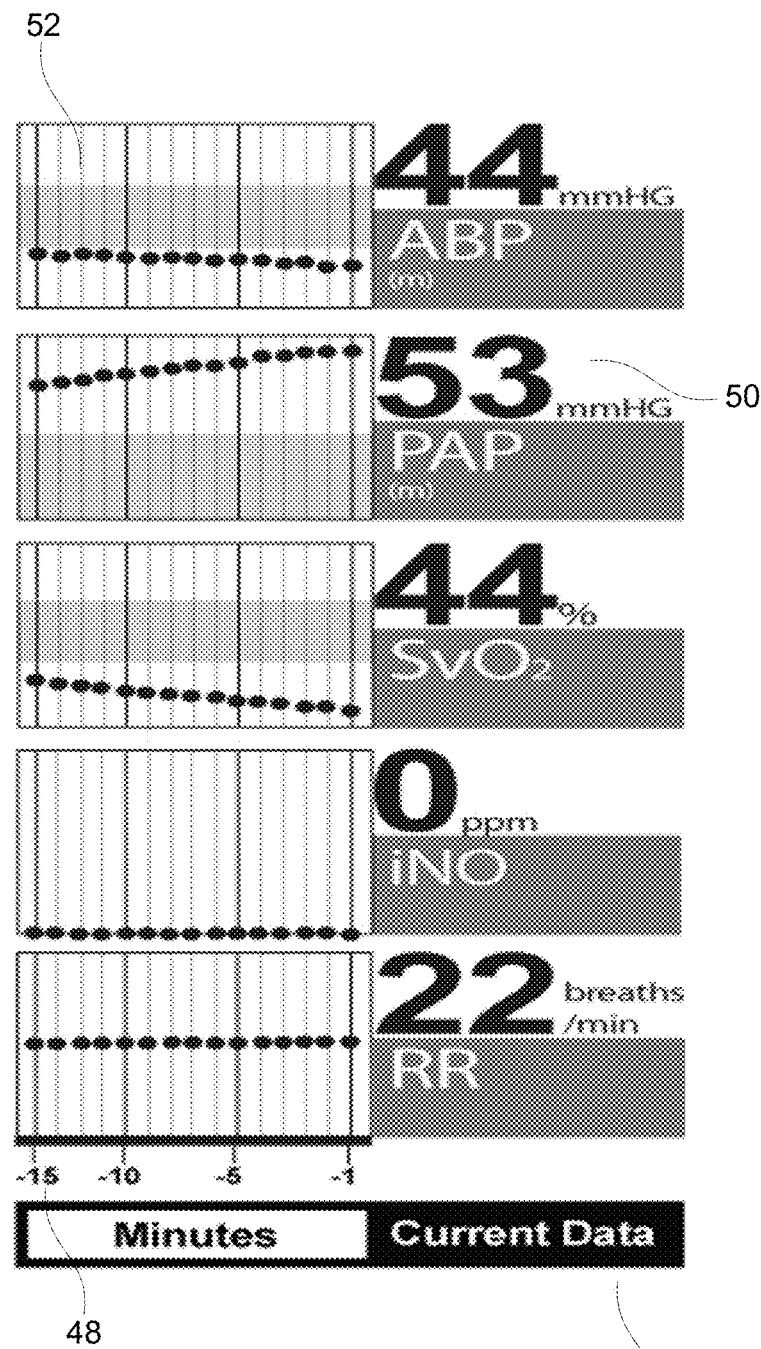
FIG. 6 is a diagram depicting yet another exemplary embodiment of the present invention.

In another embodiment (as shown in FIG. 4 generally and FIG. 6 in more detail), the medical information visualization tool may be configured to display the recent medical information on a graph 52. The graph 52 may represent a particular medical parameter during a predetermined recent time period 48. For example, in FIG. 6, this predetermined time period 48 includes the most recent 15 minutes. However, any other time period deemed to be "recent" by a medical operator may suffice. The medical information visualization tool may be further configured to simultaneously display real-time medical information as a numeric value 50. In FIG. 6, for example, these numeric values 50 include ABP=44 mmHg, PAP=53 mmHg, SvO=44%, iNO=0 ppm and RR=22 breaths/min.

In one embodiment, the medical information visualization tool may include a current data status section (CDS) 54. The CDS 54 may display the to-the-minute (real-time or near real-time) data stream. As can be seen in FIG. 6, the CDS 54 may include a large numeric display 50 that may provide the current numeric reading from a patient's monitoring device (e.g., 44 mmHG), physiological reading initials (e.g., ABP) and/or a graph 52 having compressed data points (e.g. the most recent 15 minute readings).

Figure 7:
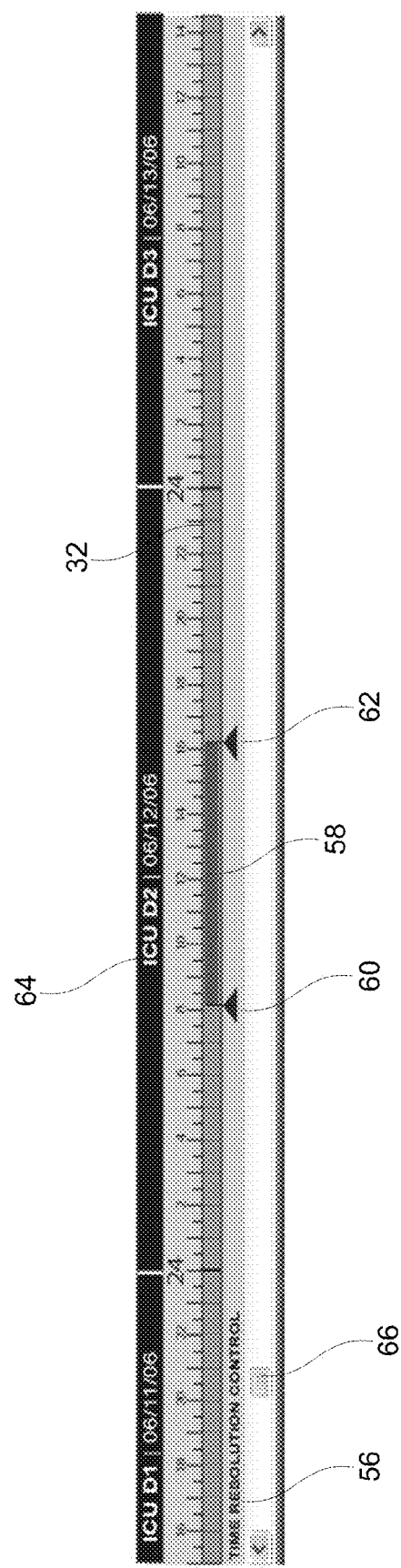
FIG. 7 is a diagram depicting an exemplary embodiment of the present invention.

In yet another embodiment (as shown in FIG. 4 generally and FIG. 7 in more detail), the medical information visualization tool may include a time resolution controller 56 configured to select a time period 58 in which the medical information is to be displayed. In FIG. 7, for example, the time period 58 is approximately 8 A.M. through 4 P.M. on June 12. This time period 58 may be adjusted by selecting a start time 60 and an end time 62 to define, redefine and/or adjust the time period 58. For example, the arrows 60, 62 shown in FIG. 7 may be moved left and right on the timeline 32 (using a touch-and-slide action on the touch screen, for example) to increase, decrease or merely shift the time period 58.

In one embodiment, the medical information visualization tool may include a time resolution control section (TRC) 56. The TRC 56 may allow the clinician to scroll left and right throughout the entire timeline 32 (including the duration of the patient's history in the medical facility), as well as to focus on specified earlier time periods 58. The TRC may include a day indicator 64 that indicates the specific day and date on the timeline 32, and a day controller slider 66 that may allow the clinician to scroll left and right throughout the entire history of the patient's stay. In this manner, if a patient is in the medical facility for several weeks, the clinician may easily scroll to find a past day and time necessary to compare with their current reading. The TRC 56 may also include a timeline 32 having a time indication area that may display each day broken down in 30 minute intervals. Clinicians may specify smaller time intervals if necessary (e.g., 15, 10, or 5 minutes). Further, the clinician may want to focus on a specific time range of four to six hours, for example, to compare to the current readings. The clinician may control the breadth of time to observe (e.g., three hours or six hours) using the beginning 60 and ending 62 time resolution control handles. These may be adjusted for the desired length of time. The clinician may also identify and compare the length of time and the location of an earlier time (within the patient's history) with the current reading, indicated at the CDS 54.

Figure 8:
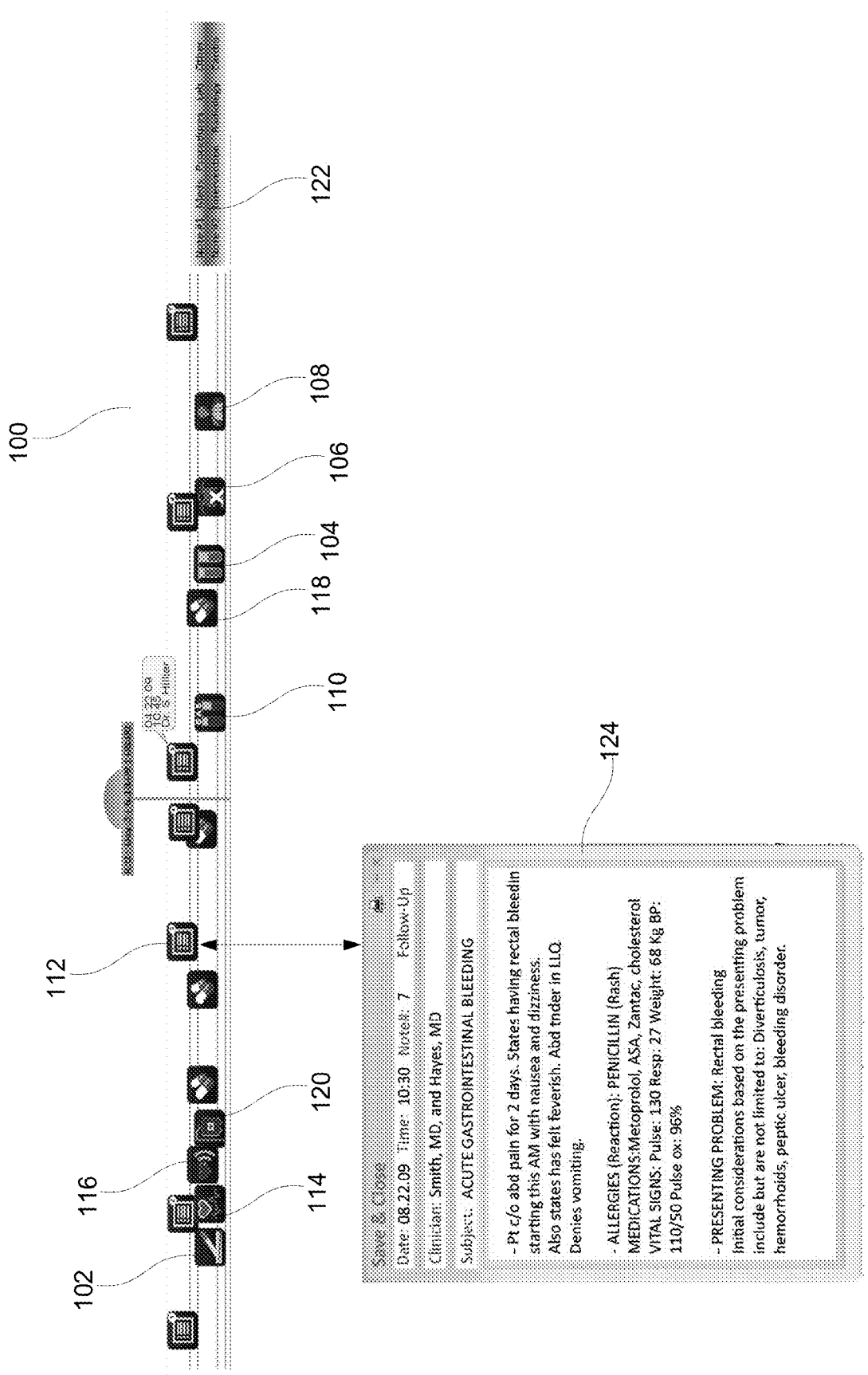
FIG. 8 is a diagram depicting an exemplary embodiment of the present invention.

In another embodiment, the medical information visualization tool (as depicted in FIG. 8) may include an icon tool controller 100 configured to display icons on or near the displayed historical medical information. These icons may be associated with a medical treatment, a medical procedure, a medical test and/or other similar event. Examples of such icons may include icons associated with operating room procedures 102, lab work 104, x-rays 106, ventilation settings changes 108, GAS lab work 110, clinician notes 112, cardio EKG 114, cardio echo 116, medication administration 118 and blood administration 120, among others. The icons may be displayed at an approximate time when the medical treatment, medical procedure, medical test and/or other similar event occurred. For example, FIG. 8 includes an icon 106 placed near the time that x-rays of the patient were taken. Alternatively, or additionally, icons may be placed on an individual parameter graph 30 (as opposed to one icon for the all parameter graphs 30). Further, icons may be graphical or textual (such as the phrase "X-Rays Taken") in nature. In one embodiment, a textual icon may be displayed to identify an abnormal condition such as a heart monitoring probe being disconnected from a patient. In that case, the textual icon may state "Heart monitoring device disconnected—patient did not flatline."

In one embodiment, the medical information visualization tool may include a clinical icon tray section (CIT) 100. The CIT 100 may provide the clinician a broad array of information about the patient's history since the time admitted into the medical facility. When an icon is placed on the timeline by a clinician, it may represent a clinical note 112 or intervention administered to the patient. Each icon may be placed within the timeline at or near the exact location (in time) where the note 112 or intervention was given.

Historical data about the patient may be represented by icons in various categories. For example, one category may be represented by Note Icons 112 that may be placed on the top bar of the CIT 100. These may be separated from the bottom of CIT 100, as there may be many notes left by clinicians throughout the stay of the patient in the medical facility. Another category may be represented by several other types of icons (as discussed above, for example) that may be placed on the bottom bar of the CIT 100. These icons may identify an array of interventions that have been administered to the patient. In one embodiment, the icons may be generated using an icon generator 122. A clinician may use a "drag and drop" movement to place icons from the icon generator 122 onto the timeline. Clinicians may also place new icons on the timeline by clicking on the icon generator 122. The respective icon may appear automatically in the timeline based on the current date and time. In such an embodiment, the clinician does not have to worry about placing the icon in the correct location on the timeline.

In one embodiment, clinician notes 112 icons may be placed on the timeline. As a clinician roll their cursor and/or finger over the clinical note 112 icon, information about the date, time, and clinician author of the note may appear in a details box 124. In another embodiment, as clinician note 112 icons are generated throughout a patient's stay, the clinician note 112 icons may be numbered consecutively. Clinicians may find the details of the clinician note 112 icon (and all other icons) by clicking on the icon, which may open a details box 124 with all the details related to date, time, clinical note or other intervention information. After creating the original note, clinicians may "save & close" the details box 124. Clinicians may also print the note using a printer. If other clinicians desire to read a note, they may activate the icon.

In another embodiment, the medical information visualization tool may include a private messaging system configured to provide inter-clinician textual communications. In one embodiment, such a private messaging system may include an inbox for received messages, an outbox for sent messages. In another embodiment, the private messaging system may provide for messages to be directed to a specific clinician. In other embodiments, the messages may be directed to any clinician who reviews the patient's medical information. A message may also be identified by a flashing icon and/or read/unread message icons upon a clinician logging into or initializing the medical information visualization tool.

Figure 9:
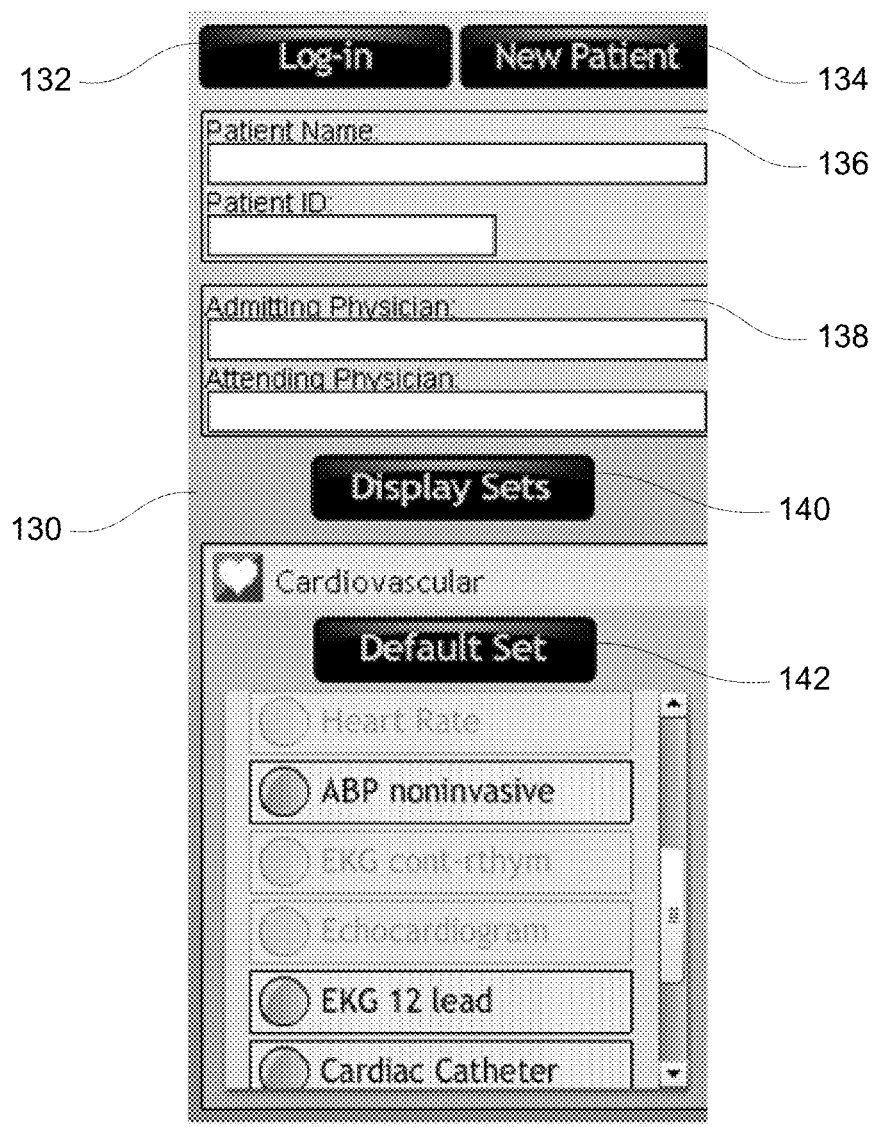
FIG. 9 is a diagram depicting an exemplary embodiment of the present invention.

In some embodiments (as depicted in FIG. 9), the medical information visualization tool may include a profile interface 130 configured to select, display and/or identify user accounts, patient accounts, clinician accounts, and/or medical parameter specialty sets. By actuating the "Log-in" button 132 (via a mouse click, finger touch or other actuation means), a clinician may log in to the medical information visualization tool. By logging in to the medical information visualization tool, the clinician may have easy access to any patients associated with that clinician. Further, each clinician may have a profile associated therewith. A clinician or patient profile may display medical parameters and/or medical specialty areas associated with that clinician or patient, respectively. For example, if the clinician is a cardiologist, the profile interface 130 may display cardiovascular medical parameters by default. Similarly, if the patient has cardiovascular problems, the profile interface 130 may display cardiovascular medical parameters by default. By actuating the "New Patient" button 134, a clinician may enter information associated with a new patient. Such information may be used to create an electronic medical record. The profile interface 130 may also be configured to display information associated with a patient in the patient information section 136 and/or information associated with a clinician/physician in the clinician information section 138.

The profile interface 130 may also include medical parameter sets associated with the clinician and/or patient. By actuating the "Display Sets" button 140, a drop down menu may be displayed. The drop down menu may display medical specialty areas (or subsets of medical specialty areas) such as Cardiovascular, Pulmonary, Infectious Disease, Medications, Auto Differential, Blood Gas Profile, Coagulation, Hemogram, Liver Function, Metabolic Profile, Metabolic Special and the like. These medical specialty areas (or subsets thereof) may be associated with specific medical parameters. For example, as is shown in FIG. 9, under the Cardiovascular set, several medical parameters may be selected, such as Heart Rate, ABP invasive, EKG cont-rythm, Echocardiogram, EKG 12 lead and Cardio Catheter. In this example, the grayed out medical parameters are already being displayed on the information visualization timeline 28. By clicking the "Default Set" button 142, the clinician may return to the medical specialty area associated with the patient or clinician.

Figure 2:
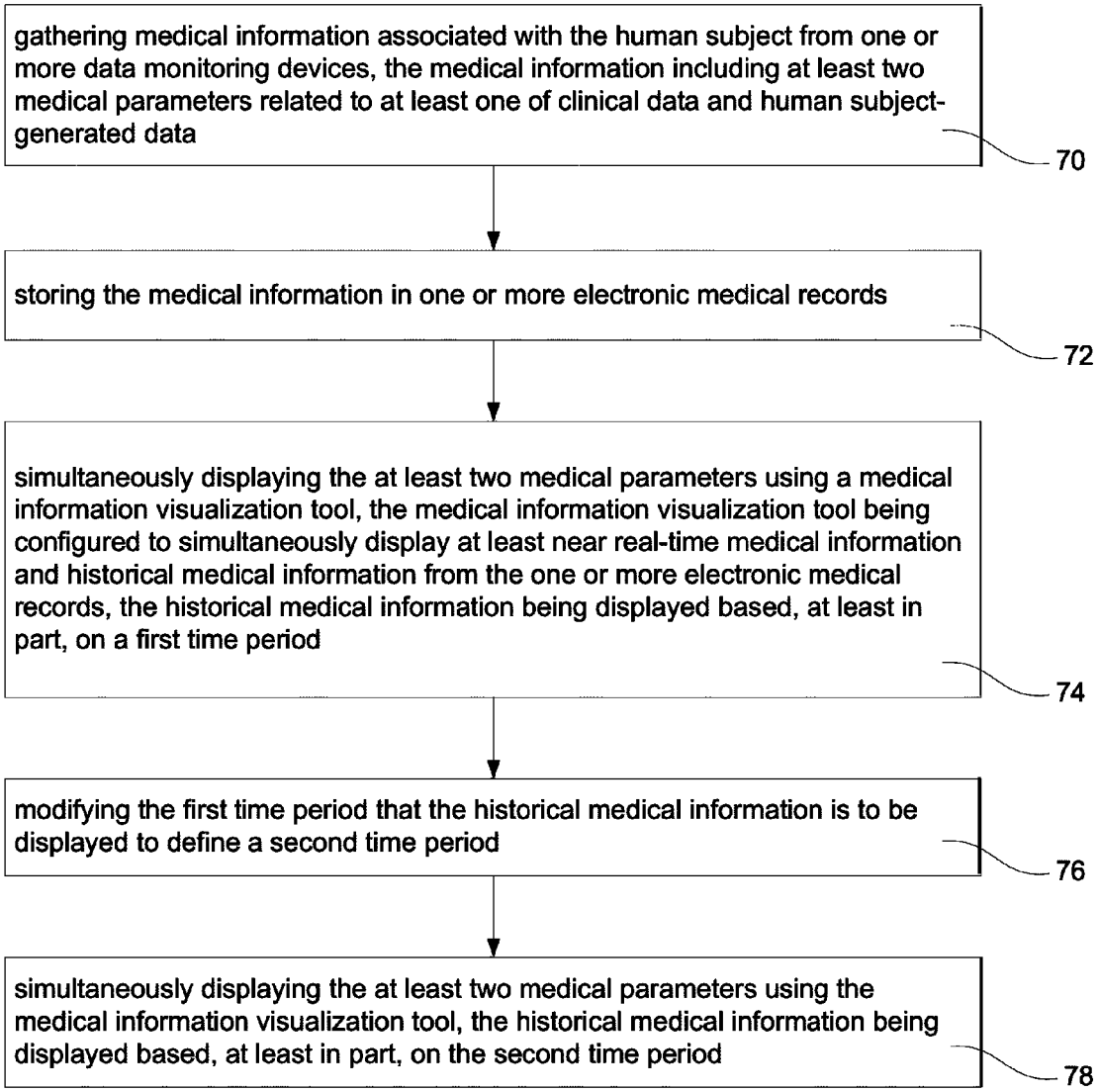
FIG. 2 is a flow diagram depicting another exemplary embodiment of the present invention.

In an exemplary embodiment (as shown in FIG. 2), a method of displaying medical information (including medical parameters) related to a human subject is provided. This method may include steps of: gathering 70 medical information associated with the human subject from data monitoring devices 14, storing 72 the medical information (or at least a sub-set of the medical information) in electronic medical record(s), simultaneously displaying 74 both real time and historical medical parameters using a medical information visualization tool, modifying 76 the time period 58 that the historical medical information is to be displayed to define another time period 58, and simultaneously displaying 78 the real time and historical medical parameters using the medical information visualization tool. In this embodiment, the medical information visualization tool may be configured to simultaneously display near real-time medical information and historical medical information from the electronic medical record(s). In another embodiment, the gathering step 70 and storing steps 72 may be performed at a predetermined time interval. In yet another embodiment, the method may also include adjusting the display order of the medical parameters using the medical information visualization tool, and simultaneously displaying the medical parameters in the adjusted display order using the medical information visualization tool.

Figure 3:
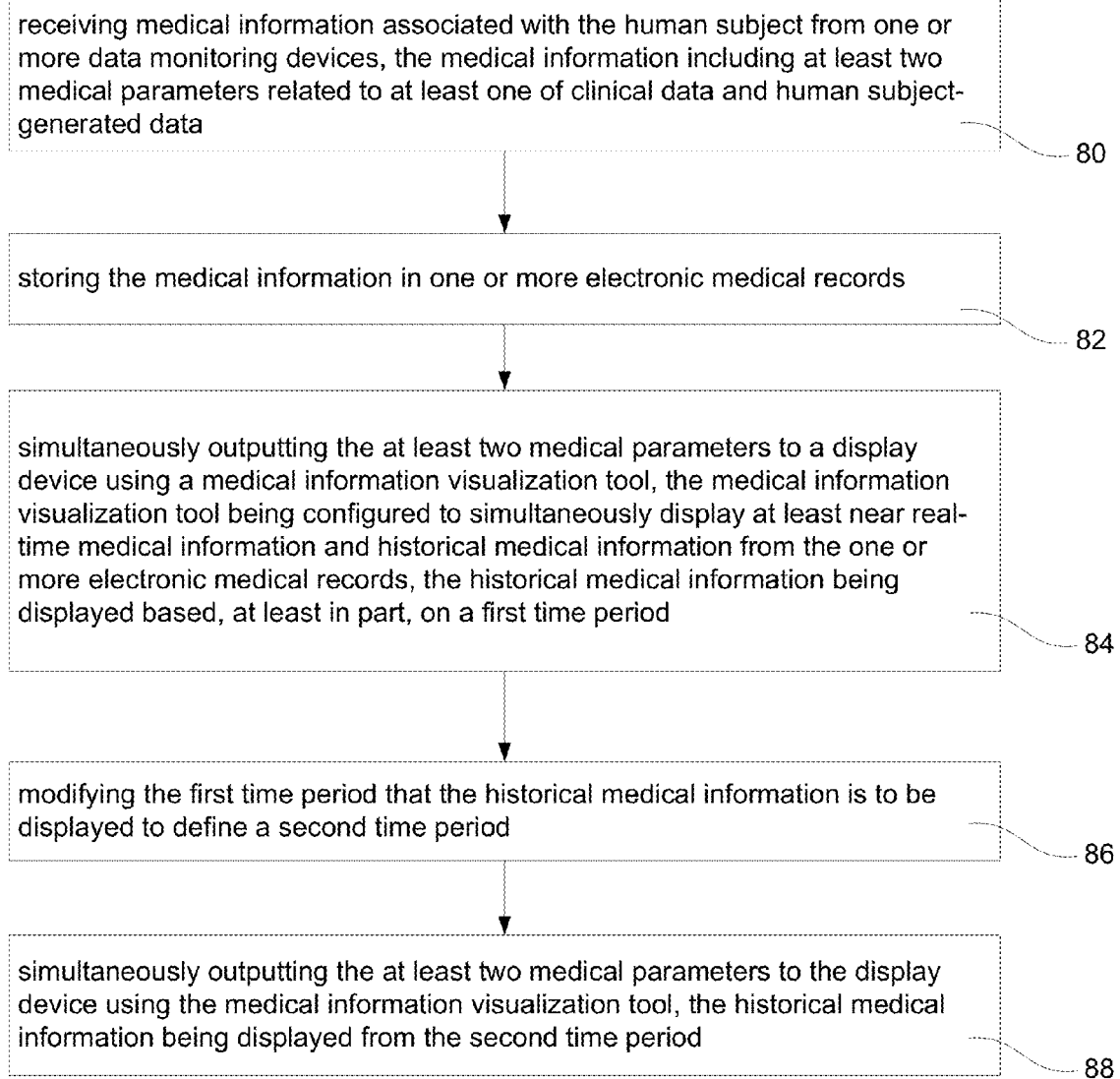
FIG. 3 is a flow diagram depicting yet another exemplary embodiment of the present invention.

In an exemplary embodiment (as shown in FIG. 3), a computer-readable medium having instructions configured to perform steps is provided. These instructions may include: receiving 80 medical information from data monitoring devices 14, storing 82 the medical information in electronic medical record(s), simultaneously outputting 84 at least two medical parameters to a display device over a first time period using a medical information visualization tool, modifying 86 the first time period that the historical medical information is to be displayed to define a second time period, and simultaneously outputting 88 the medical parameters to the display device over the second time period using the medical information visualization tool. In this embodiment, the medical information visualization tool may be configured to simultaneously display near real-time medical information and historical medical information from the electronic medical record(s).

One benefit of the medical information visualization tool may be to allow healthcare clinicians the ability to select and view several physiological data parameters in context (side-by-side, for example) while controlling the time resolution. Clinicians may be able to select and view the medical information from several perspectives. For example, these perspectives may include a clinician specific perspective (e.g. is the clinician a surgeon, anesthesiologist, etc.), a patient specific perspective (e.g. is the patient an adult or child, etc.) and/or a problem specific perspective (e.g. is the patient being treated for a heart attack or lung collapse, etc.).

In yet another embodiment, the medical information visualization tool may further include a report generation tool configured to generate one or more reports to be displayed, printed and/or transmitted. Such reports may include a complete report of all medical information or a customized report including a subset of all monitored medical information, where the subset may include only medical information chosen by a clinician. Example reports may be generated as a one-time report, a change-of-shift summary report, a daily report, an hourly report and/or other similar report.

Figure 10:
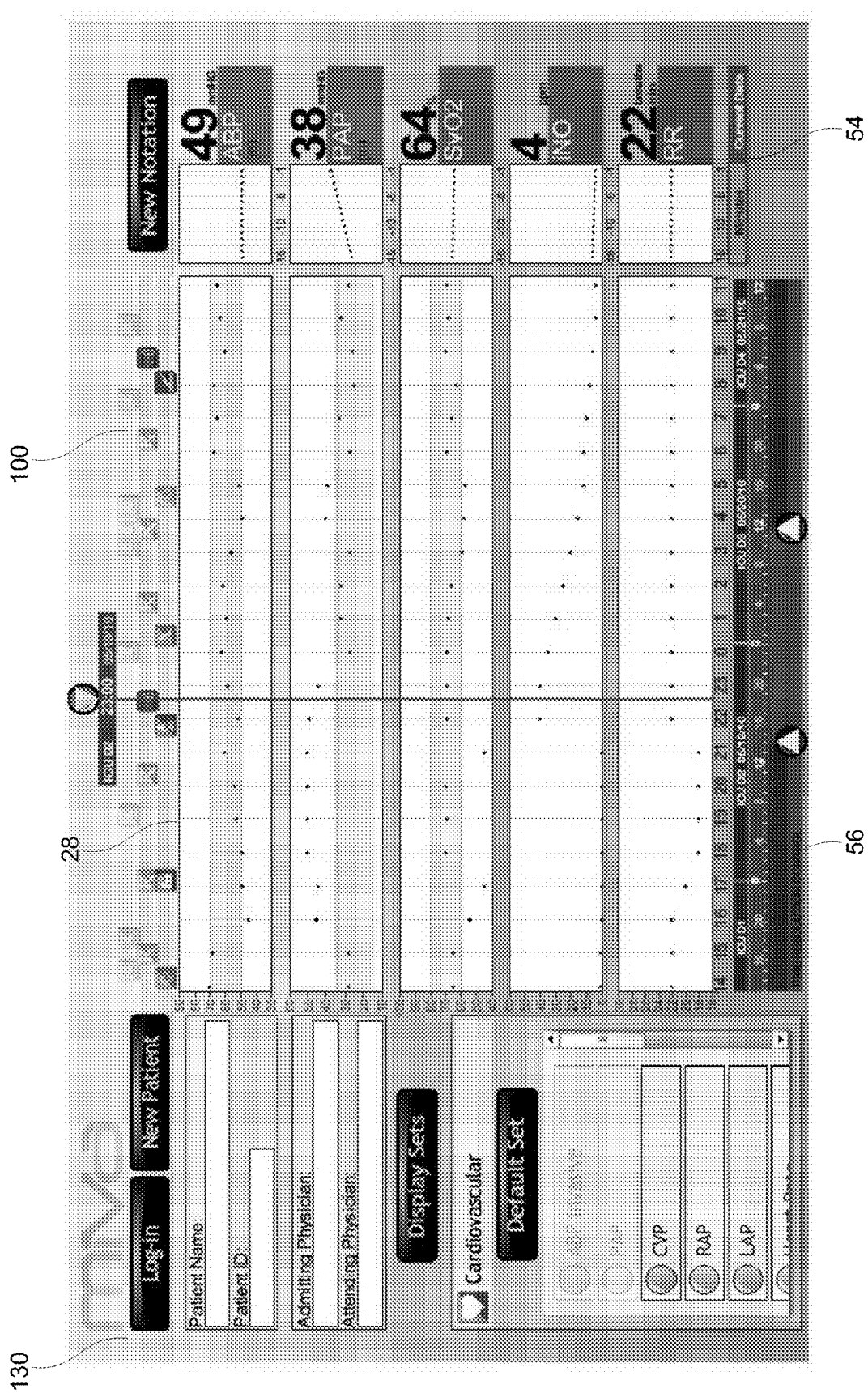
FIG. 10 is a diagram depicting an exemplary embodiment of the present invention.

In one embodiment, (as shown in FIG. 10), the medical information visualization tool may include one or more of the features described herein. For example, the medical information visualization tool may include the IVT 28, icon tool controller 100, CDS 54, TRC 56 and profile interface 130, among other features.

Figure 11:
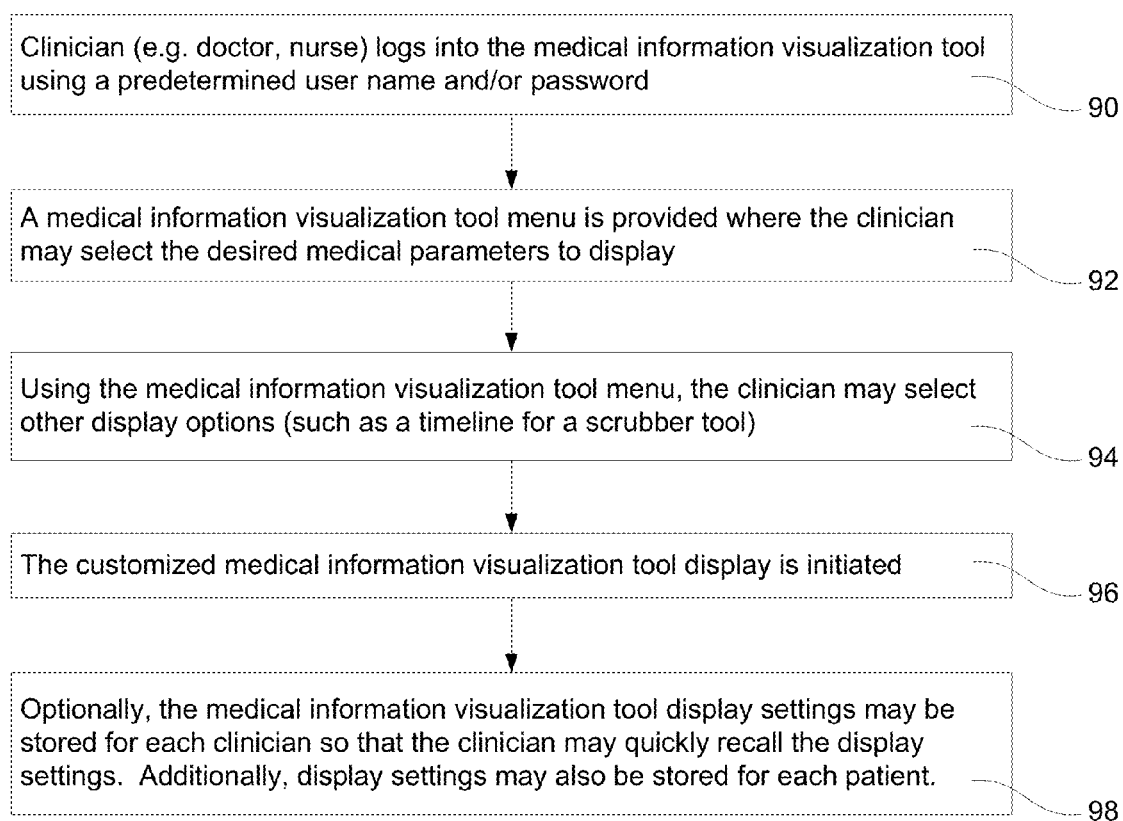
FIG. 11 is a flow diagram depicting yet another exemplary embodiment of the present invention.

In one exemplary embodiment (as shown in FIG. 11), a clinician (such as a doctor or nurse, for example) may log in 90 to the medical information visualization tool using a predetermined user name and/or password. A medical information visualization tool menu may be provided 92 where the clinician may select the desired medical parameters to be displayed on the touch-screen display. Using the medical information visualization tool menu, the clinician may select 94 other display options (such as a timeline 32 for a scrubber tool 40 or other similar options). Based, at least in part, on the medical parameters and/or display options selected, the customized medical information visualization tool display may then be initiated 96. The medical information visualization tool display settings may then be stored 98 for each clinician so that the clinician may quickly recall and reuse the display settings. Further, the medical information visualization tool display settings may also be stored 98 for each individual patient so that the clinician may quickly recall and reuse the display settings for subsequent visits by that particular patient.

To provide additional context for various aspects of the present invention, the following discussion is intended to provide a brief, general description of a suitable computing environment in which the various aspects of the invention may be implemented. One exemplary computing environment is depicted in FIG. 1. While one embodiment of the invention relates to the general context of computer-executable instructions that may run on one or more computers, those skilled in the art will recognize that the invention also may be implemented in combination with other program modules and/or as a combination of hardware and software.

Generally, program modules include routines, programs, components, data structures, etc., that perform particular tasks or implement particular abstract data types. Moreover, those skilled in the art will appreciate that aspects of the inventive methods may be practiced with other computer system configurations, including single-processor or multi-processor computer systems, minicomputers, mainframe computers, as well as personal computers, hand-held wireless computing devices, microprocessor-based or programmable consumer electronics, and the like, each of which can be operatively coupled to one or more associated devices. Aspects of the invention may also be practiced in distributed computing environments where certain tasks are performed by remote processing devices that are linked through a communications network. In a distributed computing environment, program modules may be located in both local and remote memory storage devices.

A computer may include a variety of computer readable media. Computer readable media may be any available media that can be accessed by the computer and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD ROM, digital video disk (DVD) or other optical disk storage, magnetic cassettes, magnetic tape, magnetic disk storage or other magnetic storage devices, or any other medium which may be used to store the desired information and which may be accessed by the computer.

An exemplary environment for implementing various aspects of the invention may include a computer that includes a processing unit, a system memory and a system bus. The system bus couples system components including, but not limited to, the system memory to the processing unit. The processing unit may be any of various commercially available processors. Dual microprocessors and other multi processor architectures may also be employed as the processing unit.

The system bus may be any of several types of bus structure that may further interconnect to a memory bus (with or without a memory controller), a peripheral bus, and a local bus using any of a variety of commercially available bus architectures. The system memory may include read only memory (ROM) and/or random access memory (RAM). A basic input/output system (BIOS) is stored in a non-volatile memory such as ROM, EPROM, EEPROM, which BIOS contains the basic routines that help to transfer information between elements within the computer, such as during start-up. The RAM may also include a high-speed RAM such as static RAM for caching data.

The computer may further include an internal hard disk drive (HDD) (e.g., EIDE, SATA), which internal hard disk drive may also be configured for external use in a suitable chassis, a magnetic floppy disk drive (FDD), (e.g., to read from or write to a removable diskette) and an optical disk drive, (e.g., reading a CD-ROM disk or, to read from or write to other high capacity optical media such as the DVD). The hard disk drive, magnetic disk drive and optical disk drive may be connected to the system bus by a hard disk drive interface, a magnetic disk drive interface and an optical drive interface, respectively. The interface for external drive implementations includes at least one or both of Universal Serial Bus (USB) and IEEE 1394 interface technologies.

The drives and their associated computer-readable media provide nonvolatile storage of data, data structures, computer-executable instructions, and so forth. For the computer, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules may be stored in the drives and RAM, including an operating system, one or more application programs, other program modules and program data. All or portions of the operating system, applications, modules, and/or data may also be cached in the RAM. It is appreciated that the invention may be implemented with various commercially available operating systems or combinations of operating systems.

While a touch-screen display is envisioned for at least some of the embodiments described herein, it is also within the scope of the disclosure that a user may enter commands and information into the computer through one or more wired/wireless input devices, for example, a keyboard and a pointing device, such as a mouse. Other input devices may include a microphone (functioning in association with appropriate language processing/recognition software as know to those of ordinary skill in the technology), an IR remote control, a joystick, a game pad, a stylus pen, or the like. These and other input devices are often connected to the processing unit through an input device interface that is coupled to the system bus, but may be connected by other interfaces, such as a parallel port, an IEEE 1394 serial port, a game port, a USB port, an IR interface, etc.

A display monitor or other type of display device may also be connected to the system bus via an interface, such as a video adapter. In addition to the monitor, a computer may include other peripheral output devices, such as speakers, printers, etc.

The computer may operate in a networked environment using logical connections via wired and/or wireless communications to one or more remote computers. The remote computer(s) may be a workstation, a server computer, a router, a personal computer, a portable computer, a personal digital assistant, a cellular device, a microprocessor-based entertainment appliance, a peer device or other common network node, and may include many or all of the elements described relative to the computer. The logical connections depicted include wired/wireless connectivity to a local area network (LAN) and/or larger networks, for example, a wide area network (WAN). Such LAN and WAN networking environments are commonplace in offices, and companies, and facilitate enterprise-wide computer networks, such as intranets, all of which may connect to a global communications network such as the Internet.

The computer may be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi (such as IEEE 802.11x (a, b, g, n, etc.)) and Bluetooth™ wireless technologies. Thus, the communication may be a predefined structure as with a conventional network or simply an ad hoc communication between at least two devices.

The system may also include one or more server(s). The server(s) may also be hardware and/or software (e.g., threads, processes, computing devices). The servers may house threads to perform transformations by employing aspects of the invention, for example. One possible communication between a client and a server may be in the form of a data packet adapted to be transmitted between two or more computer processes. The data packet may include a cookie and/or associated contextual information, for example. The system may include a communication framework (e.g., a global communication network such as the Internet) that may be employed to facilitate communications between the client(s) and the server(s).

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A system for displaying medical information related to a human subject, comprising:
    a computer system;
    one or more server systems in communication with the computer system;
    one or more data monitoring devices providing at least near real-time medical information to the computer system and/or the one or more server systems;
    one or more electronic medical records in communication with the one or more server systems, each electronic medical record being configured to store historical medical information associated with the human subject;
    a medical information interoperability tool in communication with the one or more electronic medical records, the medical information interoperability tool configured to translate and transmit real-time and/or historical medical information among the one or more data monitoring devices, one or more electronic medical records and the one or more server systems; and
    a medical information visualization tool stored on the one or more server systems and accessible by the computer system, the medical information visualization tool being configured to display at least near real-time medical information from the data monitoring devices and historical medical information from at least one of the electronic medical records and/or the medical information interoperability tool, the at least near real-time and historical medical information including medical parameters related to at least one of clinical data and human subject-generated data;
    wherein the medical information visualization tool includes a touch-screen operated scrubber tool that is configured to select a particular time on a timeline and to display the historical medical information on a graph having a dynamically adjustable time period, the displayed historical medical information including numeric values that are representative of the medical parameters, wherein a particular time on the timeline is selected by touching the scrubber tool on the touch-screen and sliding the scrubber tool along the timeline to a corresponding location representative of the particular time being selected;
    wherein the medical information visualization tool is configured to simultaneously display at least two parameters of the historical medical information and the at least near real-time medical information, the historical medical information being displayed on the graph having a dynamically adjustable time period; and
    wherein the medical information visualization tool is configured to allow a healthcare clinician to select and view a range of physiological data parameters for a patient over a select time period, the range of physiological data parameters being selectable and viewable from at least one customizable perspective selected from the group consisting of a clinician specific perspective, a patient specific perspective and a medical condition specific perspective.

2. The system of claim 1, wherein the medical information visualization tool is configured to be dynamically adjustable such that the at least two parameters of historical and at least near real-time medical information may be displayed in a customizable order.

3. The system of claim 1, wherein at least two parameters of historical medical information and at least near real-time medical information are displayed in a vertical orientation.

4. The system of claim 1, wherein one or more data monitoring devices includes one or more health monitoring devices temporarily affixed to the human subject, the one or more health monitoring devices adapted to continuously and/or intermittently monitor the medical parameters.

5. The system of claim 1, wherein the graph represents a particular medical parameter during a predetermined recent time period; and
    wherein the medical information visualization tool is further configured to simultaneously display real-time medical information as a numeric value.

6. The system of claim 1, wherein the medical information visualization tool includes a time resolution controller configured to select a time period in which the medical information is to be displayed.

7. The system of claim 6, wherein the time resolution controller is further configured to select a start time and an end time that defines the time period.

8. The system of claim 1, wherein the medical information visualization tool includes an icon tool controller configured to display at least one icon near the historical medical information being displayed, the at least one icon being associated with at least one of a medical treatment, a medical procedure and a medical test; and wherein the at least one icon is displayed at an approximate time that the medical treatment, medical procedure and/or medical test was performed.

9. The system of claim 1, further comprising:

a messaging system in communication with the one or more electronic medical records, the messaging system configured to provide at least one of inter-clinician textual communications and clinician note taking.

10. The system of claim 1, further comprising:

a report generation tool configured to generate one or more reports to be displayed, printed and/or transmitted, wherein the one or more reports include at least two parameters of the historical medical information and the at least near real-time medical information, the historical medical information being displayed on the graph.

11. A method of displaying medical information related to a human subject, the method comprising:

gathering medical information associated with the human subject from one or more data monitoring devices, the medical information including at least two medical parameters related to at least one of clinical data and human subject-generated data;

storing the medical information in one or more electronic medical records;

simultaneously displaying the at least two medical parameters using a medical information visualization tool, the medical information visualization tool being configured to simultaneously display at least near real-time medical information and historical medical information from the one or more electronic medical records, the historical medical information being displayed based, at least in part, on a first time period;

modifying the first time period that the historical medical information is to be displayed to define a second time period; and simultaneously displaying the at least two medical parameters using the medical information visualization tool, the historical medical information being displayed based, at least in part, on the second time period;

wherein the medical information visualization tool includes a touch-screen operated scrubber tool that is configured to select a particular time on a timeline and to display the historical medical information on a graph having a dynamically adjustable time period, the displayed historical medical information including numeric values that are representative of the at least two medical parameters, wherein a particular time on the timeline is selected by touching the scrubber tool on the touch-screen and sliding the scrubber tool along the timeline to a corresponding location representative of the particular time being selected; and wherein the medical information visualization tool is configured to allow a healthcare clinician to select and view a range of physiological data parameters for a patient over a select time period, the range of physiological data parameters being selectable and viewable from at least one customizable perspective selected from the group consisting of a clinician specific perspective, a patient specific perspective and a medical condition specific perspective.

12. The method of claim 11, wherein the gathering step and storing steps are performed at a predetermined time interval.

13. The method of claim 11, further comprising:

adjusting the display order of the at least two medical parameters to be displayed using the medical information visualization tool; and simultaneously displaying the at least two medical parameters in the adjusted display order using the medical information visualization tool.

14. A non-transitory computer-readable medium having instructions thereon, the instructions configured to perform the steps of:

receiving medical information associated with the human subject from one or more data monitoring devices, the medical information including at least two medical parameters related to at least one of clinical data and human subject-generated data;

storing the medical information in one or more electronic medical records;

simultaneously outputting the at least two medical parameters to a display device using a medical information visualization tool, the medical information visualization tool being configured to simultaneously display at least near real-time medical information and historical medical information from the one or more electronic medical records, the historical medical information being displayed based, at least in part, on a first time period;

modifying the first time period that the historical medical information is to be displayed to define a second time period; and simultaneously outputting the at least two medical parameters to the display device using the medical information visualization tool, the historical medical information being displayed based, at least in part, on the second time period;

wherein the medical information visualization tool includes a touch-screen operated scrubber tool that is configured to select a particular time on a timeline and to display the historical medical information on a graph having a dynamically adjustable time period, the displayed historical medical information including numeric values that are representative of the at least two medical parameters, wherein a particular time on the timeline is selected by touching the scrubber tool on the touch-screen and sliding the scrubber tool along the timeline to a corresponding location representative of the particular time being selected; and wherein the medical information visualization tool is configured to allow a healthcare clinician to select and view a range of physiological data parameters for a patient over a select time period, the range of physiological data parameters being selectable and viewable from at least one customizable perspective selected from the group consisting of a clinician specific perspective, a patient specific perspective and a medical condition specific perspective.

15. The non-transitory computer-readable medium of claim 14, wherein the gathering step and storing steps are performed at a predetermined time interval.

16. The non-transitory computer-readable medium of claim 14, wherein the instructions are further configured to perform the steps of:

adjusting the display order of the at least two medical parameters to be outputted using the medical information visualization tool; and simultaneously outputting the at least two medical parameters in the adjusted display order to the display device using the medical information visualization tool.

* * * * *